United States Patent [19]

Bergmeyer et al.

[11] Patent Number: 5,591,580
[45] Date of Patent: Jan. 7, 1997

[54] METHOD, TEST ELEMENT AND TEST KIT FOR SEMI-QUANTITATIVE DETECTION OF TARGET NUCLEIC ACID

[75] Inventors: Lynn Bergmeyer; Thomas J. Cummins, both of Rochester, N.Y.

[73] Assignee: Johnson & Johnson Clinical Diagnostics, Inc., Rochester, N.Y.

[21] Appl. No.: 221,818

[22] Filed: Mar. 31, 1994

[51] Int. Cl.[6] .............................. C12Q 1/68; C12P 19/34
[52] U.S. Cl. ............................................. 435/6; 435/91.2
[58] Field of Search ...................... 435/6, 91.2; 422/57, 422/68.1

[56] References Cited

U.S. PATENT DOCUMENTS

| | | | |
|---|---|---|---|
| 4,711,955 | 12/1987 | Ward et al. | 536/29 |
| 4,994,373 | 2/1991 | Stavrianopoulos et al. | 435/6 |
| 5,173,260 | 12/1992 | Zander et al. | 422/57 |
| 5,273,882 | 12/1993 | Snitman et al. | 435/6 |
| 5,374,524 | 12/1994 | Miller | 435/6 |
| 5,380,489 | 1/1995 | Sutton et al. | 422/68.1 |
| 5,387,510 | 2/1995 | Wu | 435/91.2 |

FOREIGN PATENT DOCUMENTS

| | | |
|---|---|---|
| 0370694 | 5/1990 | European Pat. Off. . |
| 370694A3 | 5/1990 | European Pat. Off. .......... C12Q 1/68 |
| 530357 | 3/1992 | European Pat. Off. . |
| WO90/08840 | 8/1990 | WIPO . |
| 90/08840 | 8/1990 | WIPO .............................. C12Q 1/68 |
| WO92/16659 | 10/1992 | WIPO . |

*Primary Examiner*—W. Gary Jones
*Assistant Examiner*—Amy Atzel

[57] ABSTRACT

A target nucleic acid can be detected in a semi-quantitative fashion by passing it over detection deposits in a test element. The detection deposits include particles affixed to the test element, some of which particles have capture probe attached thereto, and other particles having no capture probe. The deposits have varying amounts of capture probe so that the signal obtained when the target nucleic acid is captured thereon can be semi-quantitatively correlated to the amount of target nucleic acid in the specimen. This method of detection can be used in nucleic acid hybridization assays or following amplification methods, including polymerase chain reaction.

20 Claims, 1 Drawing Sheet

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH:30 nucleotides
        ( B ) TYPE:Nucleic acid
        ( C ) STRANDEDNESS:Single
        ( D ) TOPOLOGY:Linear ( i i ) MOLECULE TYPE:Capture probe ( i i i ) HYPOTHETICAL:No ( i v ) ANTI-SENSE:No ( v i ) ORIGINAL SOURCE:Synthetically prepared ( v i i ) IMMEDIATE SOURCE:Same ( x ) PUBLICATION INFORMATION:Unknown ( x i ) SEQUENCE DESCRIPTION:SEQ ID NO:1:

GAACCGAGGG CCGGCTCACC TCTATGTTGG     30

( 2 ) INFORMATION FOR SEQ ID NO:2:

( i ) SEQUENCE CHARACTERISTICS:
        ( A ) LENGTH:30 nucleotides
        ( B ) TYPE:Nucleic acid
        ( C ) STRANDEDNESS:Single
        ( D ) TOPOLOGY:Linear ( i i ) MOLECULE TYPE:Target oligonucleotide ( i i i ) HYPOTHETICAL:No ( i v ) ANTI-SENSE:No ( v i ) ORIGINAL SOURCE:Synthetically prepared ( v i i ) IMMEDIATE SOURCE:Same ( x ) PUBLICATION INFORMATION:None ( x i ) SEQUENCE DESCRIPTION:SEQ ID NO:2:

CCAACATAGA GGTGAGCCGG CCCTCGGTTC     30

METHOD, TEST ELEMENT AND TEST KIT FOR SEMI-QUANTITATIVE DETECTION OF TARGET NUCLEIC ACID

FIELD OF THE INVENTION

This invention relates to a diagnostic method, test element, and test kit useful for the semi-quantitative detection of a target nucleic acid. In particular, it relates to the use of multiple detection deposits of capture probes on a support to detect the target nucleic acid, with or without amplification, in a semi-quantitative manner.

BACKGROUND OF THE INVENTION

Technology to detect very low quantities of nucleic acids associated with various infectious agents (including viruses, bacteria, fungus and protozoa) has advanced rapidly over the last ten years. Such technology includes highly sophisticated hybridization assays using probes in conjunction with amplification techniques such as polymerase chain reaction (PCR) and ligase amplification methods. Researchers have readily recognized the value of such technology to detect diseases and genetic features in human or animal test specimens. The use of probes and primers in such technology is based upon the concept of complementarity, that is the bonding of two strands of a nucleic acid by hydrogen bonds between complementary nucleotides (also known as nucleotide pairs).

PCR is a significant advance in the art to allow detection of yew small quantities of a targeted nucleic acid. The details of PCR are described, for example, in U.S. Pat. No. 4,683,195 (Mullis et al), U.S. Pat. No. 4,683,202 (Mullis), and U.S. Pat. No. 4,965,188 (Mullis et al) and by Mullis et al, *Methods of Enzymology*, 155, pp. 335–350 (1987), although there is a rapidly expanding volume of literature in this field.

Once the target nucleic acid has been amplified, it can be detected using various techniques. Various devices have been designed for hybridization assays whereby the target nucleic acid is insolubilized prior to detection using a capture probe. For example, nitrocellulose filters and other planar, solid supports have been used to immobilize capture probes for this purpose. One technique used to attach probes to the support is to merely dry them down. More recently, they have been attached to polymeric particles which have been fused to the support (see U.S. Pat. No. 5,173,260 of Zander et al). Still again, such polymeric particles having capture probes can be adhered to supports using polymeric adhesives and various treatments of the supports, as described for example, in EP-A-0 530 357. None of these references, however, describes how such capture probes can be used for semi-quantitative detection of a target nucleic acid.

Various analytical assays, including those used with amplification methods, are based on the detection of a detectable species, such as a dye, fluorescent substance, or radioisotope on the surfaces of small (micrometer or smaller) particles. The results of such assays can be evaluated with sophisticated optical devices to provide truly quantitative results, as in the evaluation of signals generated in clinical chemistry test devices (such as EKTACHEM™ test slides). Assay results can also be read visually or with simpler equipment (such as a photometer) to merely provide a positive or negative result.

It would be highly desirable to be able to obtain a quick, semi-quantitative evaluation in an assay using simple equipment such as a photometer. By "semi-quantitative" it is meant that the detection allows for estimating that the result is within several specific ranges of absolute values. For example, it would be desirable to determine whether a target nucleic acid is present in a small, intermediate or large concentration, or simply not at all. Presently, this capability is available only using sophisticated and expensive analytical equipment and tedious procedures which require multiple dilutions of patient samples. However, most laboratories or doctors' offices do not have such equipment available.

SUMMARY OF THE INVENTION

These problems are overcome with a method for the semi-quantitative determination of a target nucleic acid comprising:

A) contacting a target nucleic acid having a specific binding ligand bound thereto with a water-insoluble support having affixed thereon a multiplicity of detection deposits, each detection deposit comprising a mixture of water-insoluble first and second particles, the first particles having affixed thereto a capture probe which is specific to and hybridizable with the target nucleic acid, and the second particles being free of the capture probe, the multiplicity of detection deposits having a varying weight ratio of the first particles to the second particles, but all of the detection deposits having about the same total weight of polymeric particles and the same configuration, to capture the target nucleic acid strand on the detection deposits in proportion to the amount of the first particles in each detection deposit, B) contacting the captured target nucleic acid strand in the detection deposits with a receptor for the specific binding ligand, the receptor being labeled with a reporter molecule, to complex the reporter labeled receptor with the captured target nucleic acid strand and thereby capture the reporter labeled receptor on each of the detection deposits in proportion to the amount of captured ligand labeled target nucleic acid strand in each of the detection deposits, and C) detecting the reporter molecules on the detection deposits as a semi-quantitative determination of the presence of the target nucleic acid.

Further, a method for the amplification and semi-quantitative determination of a target nucleic acid comprises:

A) amplifying opposing strands of a target nucleic acid with a DNA polymerase, more than one dNTP and a set of two primers specific to and hybridizable with the opposing strands, one of the primers being labeled with a specific binding ligand, thereby providing at least one amplified ligand labeled strand of the target nucleic acid, B) contacting the amplified ligand labeled target nucleic acid strand with a water-insoluble support having affixed thereon a multiplicity of detection deposits, each detection deposit comprising a mixture of water-insoluble first and second particles, the first particles having affixed thereto a capture probe which is specific to and hybridizable with the ligand labeled target nucleic acid strand, and the second particles being free of the capture probe, the multiplicity of detection deposits having a varying weight ratio of the first particles to the second particles, but all of the detection deposits having about the same total weight of polymeric particles and the same configuration, to capture the ligand labeled target nucleic acid strand on the detection deposits in proportion to the amount of the first particles in each detection deposit, C) contacting the captured ligand labeled target nucleic acid strand in the detection deposits with a receptor for the specific binding ligand, the receptor being labeled with a reporter molecule, to complex the reporter labeled receptor with the captured ligand labeled target nucleic acid strand and thereby capture the reporter labeled receptor on each of the detection deposits in proportion to the amount of captured ligand labeled target nucleic acid strand in each of the detection deposits, and D) detecting the reporter molecules on the detection deposits as a semi-quantitative determination of the presence of the target nucleic acid.

Also provided by this invention is a test element comprising a water-insoluble support having affixed thereon a multiplicity of detection deposits, each detection deposit comprising a mixture of water-insoluble first and second particles, the first particles having affixed thereto a capture probe which is specific to and hybridizable with a ligand labeled target nucleic acid, and the second particles being free of the capture probe, the multiplicity of detection deposits having a varying weight ratio of the first particles to the second particles, but all of the detection deposits having about the same total weight of polymeric particles and the same configuration.

Further, a kit for the detection of a target nucleic acid labeled with a specific binding ligand comprises:

a) either an amplification reagent, or a reporter labeled receptor for the specific binding ligand, and b) a test element as described above.

The present invention provides a simple, effective and efficient means for semi-quantitative detection of a target nucleic acid, with or without amplification. The use of sophisticated detection equipment can be avoided. These advantages are achieved by using a multiplicity of detection deposits on a support, which deposits have varying predetermined amounts of capture probe. One way of looking at the detection deposits is that the capture probe is present at various "dilutions" in the deposits so that the target nucleic acid is contacted with a series of capture probes in various amounts. The detection deposits can be arranged so that an approximation can be made of the amount of target nucleic acid by evaluation of the intensity, number or location of signals from the deposits. The capture probe is "diluted" in the detection deposits by having varying amounts of two types of particles in the deposits. One type of particle has capture probe attached thereto, while the second type of particle does not have any capture probe. However, the various detection deposits have about the same total weight of particles and the same configuration so that the signals from the array of detection deposits provide information in a semi-quantitative fashion.

A signal is not observed where no analyte is present, and where there is a low concentration of analyte, only the deposits having high amounts of capture probe will show a signal. Additional deposits of decreasing amounts of capture probe will provide a signal as the amount of analyte increases. Thus, for example, if 10 deposits of varying amounts of capture probe are used, when analyte concentration is low, only 1 or 2 deposits having the highest amount of capture probe will give a signal. As the amount of analyte increases in a specimen, more of the deposits provide a signal and therefore one can determine a semi-quantitative (or relative amount) amount of analyte.

This invention is advantageous because specimen samples need not be diluted to differentiate among signals. Thus, discrimination among signals can be more readily achieved without tedious assay procedures which require considerable time and are susceptible to operator error.

DETAILED DESCRIPTION OF THE INVENTION

Figure 1:
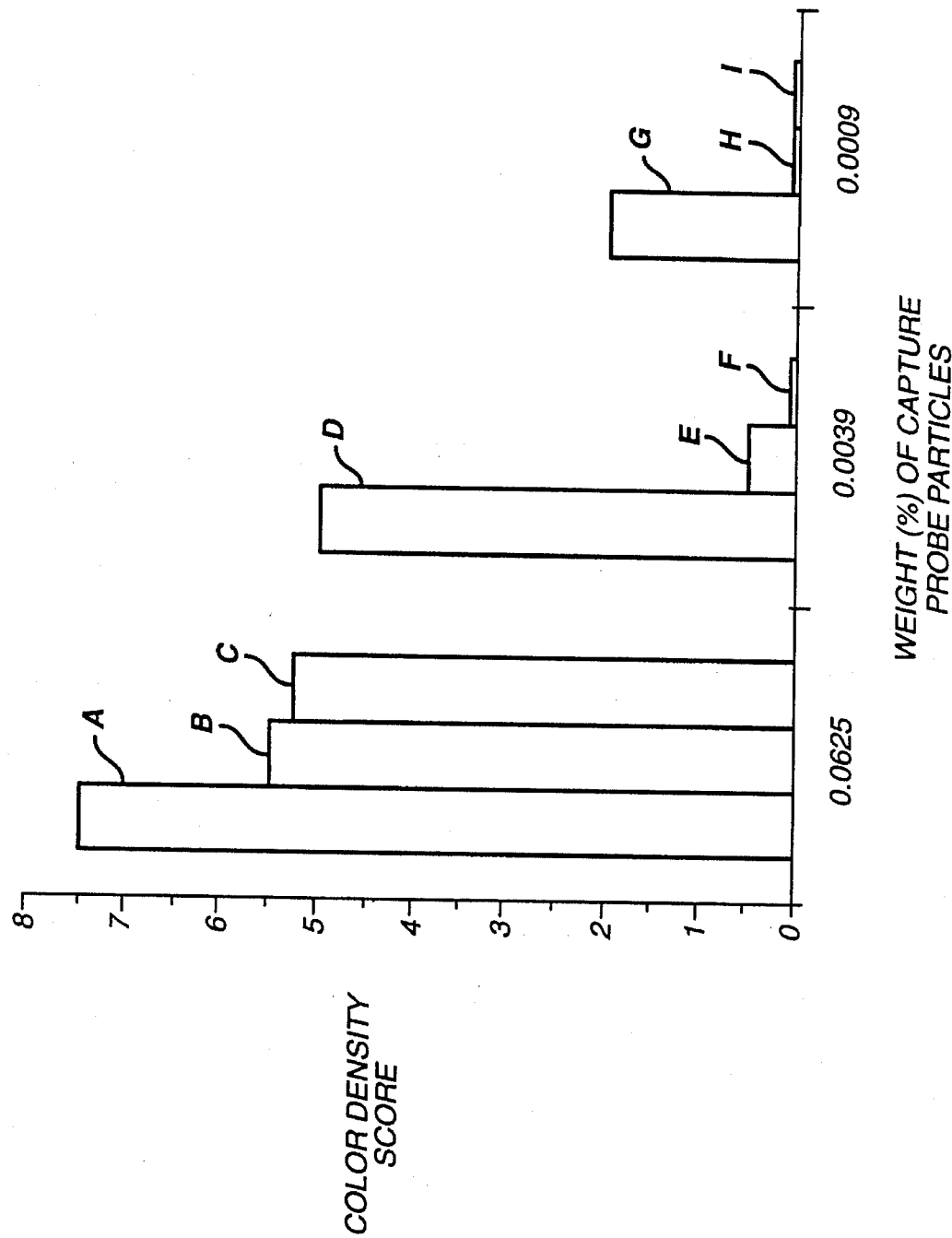
FIG. 1 contains bar graphs of the amount of dye signal observed with varying amounts of analyte using an element of this invention as described in more detail in Example 1 below.

The methods, elements and test kits of the present invention can be used in the detection of any nucleic acid using standard nucleic acid amplification and hybridization technology and appropriate detection probes conjugated with a specific binding ligand (defined below). The reagents and protocols for nucleic acid hybridization assays are well known in the art so the details thereof are not provided herein. Representative descriptions of such assays are provided in the following patents, all of which are incorporated herein by reference with respect to the details of the assays, reagents and amounts useful therein, protocols and various uses of such assays (including diagnostics, therapeutics, sequencing, detection of mutations and other uses readily apparent in the art): U.S. Pat. No. 4,358,535 (Falkow et al), U.S. Pat. No. 4,486,539 (Ranki et al), U.S. Pat. No. 4,727,019 (Valkirs et al), U.S. Pat. No. 4,994,373 (Stavrianopoulos et al) and U.S. Pat. No. 4,711,955 (Ward et al). The remaining discussion herein will be directed to the preferred embodiments of using the present invention after amplification techniques have been applied.

The present invention can be used for detection of nucleic acids after any of the known amplification techniques. Polymerase chain reaction (PCR) is the most common amplification technique, but the invention is not so limited. For example, the invention can be used with transcription based amplification techniques as described by Kwoh et al, *Proc.Nat'l.Acad.Sci.USA*, 87, 1974 (1989), nucleic acid ligase techniques described for example by Wu et al, *Genomics*, 4, 560 (1989) and Barringer et al *Gene*, 89, 117 (1990), Q-beta replicase techniques as described in U.S. Pat. No. 5,112,734 (Kramer et al), ribonuclease H cleavage of DNA-RNA probes annealed to nucleic acid targets and strand displacement assays.

The general principles and conditions for amplification and detection of nucleic acids using PCR are quite well known, the details of which are provided in numerous references including U.S. Pat. No. 4,683,195, U.S. Pat. No. 4,683,202, U.S. Pat. No. 4,965,188, the disclosures of which are incorporated herein by reference. The amplification procedures can include what is known as "nested PCR" (that is, using "nested primers" in sequence), or non-nested PCR (using the same primers throughout the process).

The present invention is directed to the amplification and semi-quantitative detection (or determination) of one or more specific nucleic acid sequences of one or more nucleic acids in a test specimen. Such specimens can include bacterial or viral material, hair, body fluids or cellular materials containing a nucleic acid which can be detected. In particular, nucleic acids to be amplified and detected can be obtained from various sources including plasmids and naturally occurring DNA or RNA from any source (such as bacteria, yeast, viruses, plants, higher animals and humans). It may be extracted from various tissues including peripheral blood mononuclear cells and other blood components, tissue material (for example, biopsy samples or exfoliated cells) or other sources known in the art using known procedures.

Bacteria which can be detected include, but are not limited to, bacteria found in human blood, Salmonella species, Streptococcus species, Chlamydia species, Gonococcal species, *Mycobacterium tuberculosis, Mycobacterium fortuitum, Mycobacterium avium complex, Legionella pneumophila, Clostridium difficile, Borrelia burgdorferi, Pneumocystis carinii, Mycoplasma, Haemophilus influenzae,* Shigella species and Listeria species. Viruses which are detectable, besides cytomegalovirus, include, but are not limited to, herpes, Epstein Barr virus, influenza viruses, human papilloma virus, hepatitis and retroviruses such as HTLV-I, HTLV-II, HIV-I and HIV-II. Protozoan parasites, yeasts and molds are also detectable. Other detectable species would be readily apparent to one skilled in the art.

A "target" DNA as used in this application also includes nucleic acids which are added to a test specimen to provide positive controls in an assay.

A "PCR reagent" refers to any of the reagents considered essential to PCR, namely primers for the target nucleic acid, a thermostable DNA polymerase, a DNA polymerase cofactor, and two or more (preferably, four) deoxyribonucleoside-5'-triphosphates. Other optional reagents and materials used in PCR are described below.

The term "primer" refers to an oligonucleotide, whether naturally occurring or synthetically produced, which is capable of acting as a point of initiation of synthesis when placed under conditions in which synthesis of a primer extension product complementary to a nucleic acid strand (that is, template) is induced. Such conditions include the presence of nucleotides (such as the four standard deoxyribonucleoside-5'-triphosphates), a thermostable DNA polymerase and a DNA polymerase cofactor, and suitable temperature and pH.

The primer is preferably single stranded for maximum efficiency in amplification, but can contain a double stranded region if desired. It must be long enough to prime the synthesis of extension products in the presence of the DNA polymerase. The exact size of each primer will vary depending upon the use contemplated, the complexity of the targeted sequence, reaction temperature and the source of the primer. Generally, the primers used in this invention will have from 12 to 60 nucleotides, and preferably, they have from 20 to 40 nucleotides.

The primers used in the present invention are selected to be "substantially complementary" to the specific nucleic acid sequences to be primed and amplified. This means that they must be sufficiently complementary to hybridize with the respective nucleic acid sequences to form the desired hybridized products and then be extendible by a DNA polymerase. In the preferred and most practical situation, the primers have exact complementarity to the nucleic acid sequences of interest.

Primers useful for the amplification and detection of additional target nucleic acids would be readily determinable by a skilled worker in the art by consultation with the considerable literature in this field to determine appropriate nucleic acid sequences of target nucleic acids. Those sequences can then be used as patterns for preparing primers using known technology. For example, primers can be prepared using known techniques and equipment such as an ABI DNA Synthesizer (available from Applied Biosystems) or a Biosearch 8600 Series or 8800 Series Synthesizer (available from Milligen-Biosearch, Inc.). Procedures for using this equipment are well known and described for example in U.S. Pat. No. 4,965,188 (noted above). Naturally occurring primers isolated from biological sources may also be useful (such as restriction endonuclease digests).

As used herein, a "probe" is an oligonucleotide which is substantially complementary to a nucleic acid sequence of the target nucleic acid and which is used for capture of the amplified target nucleic acid. The probes generally have from 10 to 40 nucleotides, although shorter or longer probes may be useful in certain assays.

Probes useful for the capture of additional target nucleic acids would be readily apparent to one skilled in the art if the targeted nucleic acid sequences are known. Many such sequences are known in the literature. Thus, the practice of this invention is adequately enabled by knowing those sequences and following the representative teaching herein regarding primers and probes actually shown. Presently unknown target nucleic acids can also be similarly amplified and detected because this technology could predictably be used in a similar fashion. Such probes can be prepared using the same procedures and starting reagents described for primers above.

The PCR reagents can be provided individually, as part of a test kit, in reagent chambers of a test device, or in admixture in a reaction composition.

Many useful DNA polymerases are well known. They are enzymes which will add deoxynucleoside monophosphate molecules to the 3' hydroxy end of the primer in a complex of primer and template, but this addition is in a template dependent manner (that is, dependent upon the specific nucleotides in the template). Synthesis of extension products proceeds in the 5' to 3' direction of the newly synthesized strand until synthesis is terminated. The DNA polymerase is preferably "thermostable" meaning that it is stable to heat and preferentially active at higher temperatures, especially the high temperatures used for priming and extension of DNA strands.

A number of thermostable DNA polymerases have been reported in the art, including those mentioned in detail in U.S. Pat. No. 4,965,188 and U.S. Pat. No. 4,889,818 (Gelfand et al), both incorporated herein by reference. Particularly useful polymerases are those obtained from various Thermus bacterial species, such as *Thermus aquaticus, Thermus thermophilus, Thermus filiformis* or *Thermus flavus*. Other useful thermostable polymerases are described in WO-A-89/06691 (published Jul. 27, 1989). Some useful polymerases are commercially available. A number of techniques are known for isolating naturally-occurring polymerases from organisms, and for producing recombinant forms using genetic engineering techniques, as noted in the art cited in this paragraph and as also described in EP-A-0 482 714 (published Apr. 29, 1992).

A DNA polymerase cofactor refers to a nonprotein compound on which the enzyme depends for activity. A number of such materials are known cofactors including manganese and magnesium compounds which contain the manganese or magnesium as divalent cations. Useful cofactors include, but are not limited to, manganese and magnesium salts, such as chlorides, sulfates, acetates and fatty acid salts (for example, butyric, caproic, caprylic, capric and lauric acid salts). The chlorides, sulfates and acetates are preferred.

Also needed for PCR are two or more deoxyribonucleoside-5'-triphosphates (dNTPs), such as dATP, dCTP, dGTP, dTTP or dUTP. Analogues such as dITP and 7-deaza-dGTP are also useful. The preferred materials, dATP, dCTP, dGTP and dTTP, are used collectively in the assays.

The PCR reagents described herein are provided and used in PCR in any concentration suitable for a given process. The minimal amounts of primers, thermostable DNA polymerase, cofactors and deoxyribonucleotide-5'-triphosphates needed for amplification and suitable ranges of each are well known in the art. Preferably, from about 0.1 to about 50 units of thermostable DNA polymerase per 100 μl of reaction mixture are used for PCR. A "unit" is defined herein as the amount of enzyme activity required to incorporate 10 nmoles of total nucleotides (dNTP's) into an extending nucleic acid chain in 30 minutes at 74° C. The amount of primer is at least about 0.075 μmolar with from about 0.1 to about 2 μmolar being preferred, but other amounts are well known in the art. The cofactor is generally present in an amount of from about 2 to about 15 mmolar. Each dNTP is present at from about 0.25 to about 3.5 mmolar.

The PCR reagents are used in admixture in an aqueous composition which is preferably buffered to a pH of from about 7 to about 9 using one or more suitable buffers including, but not limited to, tris(hydroxymethyl)aminomethane (or salts thereof).

A particularly useful composition is a buffered mixture of the primers noted herein, a magnesium cofactor as noted above, each of dATP, dCTP, dGTP and dTTP as noted above, gelatin or a similar hydrophilic colloidal material (in an amount of at least about 5%, by weight), and an alkali metal salt (such as sodium chloride or potassium chloride) present in an amount of from about 10 to about 100 mmolar. More preferably, this composition also includes an appropriate amount of a thermostable DNA polymerase (as described above) and a monoclonal antibody to such DNA polymerase, which antibody inhibits its enzymatic activity at temperatures below about 50° C., but which antibody is deactivated at higher temperatures. Representative monoclonal antibodies are described in recently allowed U.S. Ser. No. 07/958,144 (filed Oct. 7, 1992 by Scalice et al) incorporated herein by reference. Two such monoclonal antibodies are readily obtained by a skilled artisan using conventional procedures, and starting materials including either of hybridoma cell lines HB 11126 and 11127 deposited with the American Type Culture Collection (Rockville, Md.). The monoclonal antibody is present in an amount of from about 5:1 to 500:1 molar ratio to the DNA polymerase.

A target nucleic acid can be obtained from any of a variety of sources as noted above, such as a whole blood sample. Generally, it is extracted in some manner to make it available for contact with the primers and other PCR reagents. This usually means removing unwanted proteins and cellular matter from the specimen in a suitable manner. Various procedures are known in the art, including those described by Laure et al in *The Lancet*, pp. 538–540 (Sep. 3, 1988), Maniatis et al, *Molecular Cloning: A Laboratory Manual*, pp. 280–281 (1982), Gross-Belland et al in *Eur.J.Biochem.*, 36, 32 (1973) and U.S. Pat. No. 4,965,188. Extraction of DNA from whole blood or components thereof are described, for example, in EP-A-0 393 744 (published Oct. 24, 1990), Bell et al, *Proc. Natl. Acad. Sci. USA*, 78(9), pp. 5759–5763 (1981) and Saiki et al, *Bio/Technology*, 3, pp. 1008–1012 (1985).

Since the nucleic acid to be amplified and detected is usually in double stranded form, the two strands must be separated (that is, denatured) before priming can take place. This can occur during the extraction process, or be a separate step afterwards. Denaturation is accomplished using a heat treatment alone or in combination with any suitable other physical, chemical or enzymatic means as described in the art. Initial denaturation is generally carried out by heating the specimen suspected of containing the targeted nucleic acid at a first temperature of from about 85° to about 100° C. for a suitable time, for example from about 1 second to 3 minutes.

The denatured strands are then cooled to a second temperature which is generally in the range of from about 55° to about 70° C. for priming the strands. The time needed for cooling the denatured strands will vary depending upon the type of apparatus used for the PCR process.

Once the denatured strands are cooled to the second temperature, the reaction mixture containing PCR reagents is incubated at a suitable temperature to effect formation of primer extension products. Generally, this temperature is at least about 50° C., and preferably in the range of from about 62° to about 75° C. The time for incubation can vary widely depending upon the incubation temperature and the length of extension products desired, but in preferred embodiments, it is from about 1 to about 120 seconds. Each cycle of PCR can be carried out using either two or three different temperatures, one for denaturation, and a second and/or third temperature for priming and/or primer extension product formation. That is, some PCR processes utilize a second temperature for priming and a third temperature for primer extension.

If the hybridized primer extension products are then denatured, PCR can be carried out further in as many cycles of priming, extension and denaturation as desired. Generally, at least 20 cycles will be carried out, with from 20 to 50 cycles being preferred.

The amplification method of this invention is preferably conducted in a continuous, automated manner so that the reaction mixture is temperature cycled in a controlled manner for desired preset times. A number of instruments have been developed for this purpose, as one of ordinary skill in the art would know.

One such instrument for this purpose is described in some detail in U.S. Pat. No. 4,965,188 and EP-A-0 236 069. Generally, this instrument includes a heat conducting container for holding a number of reaction tubes containing reaction mixture, a means for heating, cooling and temperature maintenance, and a computing means to generate signals to control the amplification process, changes in temperature and timing.

A preferred instrument for processing amplification reactions in a disposable chemical test pack is described in some detail in U.S. Pat. No. 5,089,233 (Devaney et al), incorporated herein by reference. In general, this instrument comprises a surface for supporting one or more chemical test packs, pressure applicators supported above the surface for acting on the reaction pack to transfer fluids between adjacent chambers in the test pack, and means for operating the pressure applicators through a range of movements extending across the test pack.

EP-A-0 402 994 provides details of useful chemical test packs which can be processed using the instrument described in U.S. Pat. No. 5,089,233 (noted above). Also described therein are means for heating and cooling the test pack at repeated intervals (that is, through cycles) appropriate for the method of the present invention.

Further details regarding useful PCR processing equipment can be obtained from the considerable literature in this field, and would be readily ascertained by one skilled in the art.

It is also useful for the method of this invention to be carried out in a suitable container. The most crude container would be a test tube, cuvette, flask or beaker, but more sophisticated containers have been fashioned in order to facilitate automated procedures for performing the method (see for example, WO-A-91/12342). For example, cuvette and chemical test packs (also known as pouches), constructed to provide certain temperature characteristics during the practice of the method, are described in U.S. Pat. No. 4,902,624 (Columbus et al), U.S. Pat. No. 5,173,260 (Zander et al) and U.S. Pat. No. 5,229,297 (Schnipelsky et al), all incorporated herein by reference. Such test packs have a multiplicity of reagent chambers having various reagents, buffers and other materials which are useful at various stages in the amplification or detection method. The aqueous composition containing PCR reagents can be incorporated into a reaction chamber for use in the method of this invention. The packs can be appropriately and rapidly heated and cooled in cycles to promote the various steps of the amplification method.

Detection of the amplified target nucleic acid is accomplished using specific binding pairs. One or both of the primers used in amplification is labeled with a specific binding ligand. Thus, during amplification, the target nucleic acid molecules are labeled with the specific binding ligand. Such labels include any molecule for which there is a receptor molecule that reacts specifically with the specific binding ligand. Examples of specific binding pairs (one of which can be the label) include, but are not limited to, avidin/biotin, streptavidin/biotin, sugar/lectin, antibody/hapten, antibody/antigen and others readily apparent to one skilled in the art. A preferred specific binding ligand is biotin, and the corresponding receptor is streptavidin. The receptor is conjugated with a detectable label or reporter molecule, such as an enzyme, radioisotope or chemiluminescent reagent (for example, luminol) using known technology.

Procedures for attaching labels to receptor molecules are well known in the art, for example, as described by Agrawal et al, *Nucleic Acid Res.*, 14, pp. 6227–45 (1986) and U.S. Pat. No. 4,914,210 (Levenson et al) relating to biotin labels, U.S. Pat. No. 4,962,029 (Levenson et al) relating to enzyme labels. Other useful labels include radioisotopes, electron-dense reagents, chromogens, fluorogens, phosphorescent moieties, ferritin and other very small magnetic particles sometimes known as "ferrofluids" (U.S. Pat. No. 4,795,698 of Owen et al) and chemiluminescent moieties. Preferred enzyme labels include, glucose oxidase, peroxidases, uricase, alkaline phosphatase and others known in the art. Substrate reagents which provide a chemiluminescent or colorimetric signal in the presence of a particular enzyme label would be readily apparent to one skilled in the art since such systems have been used in clinical chemistry, immunology or nucleic acid hybridization assays for several decades. Many of such reagents are commercially available.

Where the label for the receptor is a preferred enzyme such as a peroxidase, at some point in the assay, hydrogen peroxide and a suitable dye-forming composition can be added to provide a detectable dye (that is, a colorimetric signal). For example, useful dye-providing reagents include tetramethylbenzidine and derivatives thereof, and leuco dyes, such as triarylimidazole leuco dyes (as described in U.S. Pat. No. 4,089,747 of Bruschi), or other compounds which react to provide a dye in the presence of peroxidase and an oxidant such as hydrogen peroxide. Particularly useful dye-providing compositions are described in U.S. Pat. No. 5,024,935 (McClune et al), incorporated herein by reference. Chemiluminescent signals can be generated using acridinium salts or luminol and similar compounds in combination with enhancers in the presence of peroxidase and an oxidant.

Most preferably, one or both primers are labeled with biotin (or an equivalent derivative thereof), and the amplified target nucleic acid is detected using a conjugate of streptavidin with an enzyme. The enzyme thusly attached to the specific binding complex is then detected using the appropriate substrate reagents. Peroxidase is the most preferred label for the receptor molecule.

In order for the amplified target nucleic acid to be detected, it is often useful (but not necessary) for it to be separated from the other materials in the reaction medium. This is done with a capture reagent having a capture probe which is covalently attached to a water-insoluble particle. The capture probe hybridizes with the amplified target nucleic acid and the captured material can then be separated from unhybridized materials in a suitable manner, such as by filtration, centrifugation, washing or other suitable separation techniques.

The present invention utilizes a multiplicity of detection deposits containing capture probes in order to provide a semi-quantitative determination of the target nucleic acid (whether amplified or not). The detection deposits are disposed on a water-insoluble support of any suitable material which is inert to reagents. Such supports include generally flat materials such as polymeric membranes, filter papers, glass, fibrous mats, ceramic chips, resin-coated or uncoated polymeric films, and resin-coated or uncoated papers, all of which are known in the art. Particularly useful supports are resin-coated papers or polymeric films which are sealable with themselves by heat or ultrasonic sealing means, as described for example, in EP-A-0 408 738 (published Jan. 23, 1991) and microporous polyamide membranes such as those marketed by Pall Corporation under the marks LOPRODYNE™ or BIODYNE™.

The detection deposits are affixed to the supports in any suitable manner, including drying down samples of an aqueous suspension of the particles and capture probe such as described in WO 92/16659 (published Oct. 1, 1992). Alternatively, the deposits can be secured to the support by fusing the particles into the support which may be softened by heat as described, for example, in U.S. Pat. No. 5,173,260 (Zander et al).

More preferably, the capture probes are deposited on supports as particulate reagents in admixture with a polymeric adhesive (described in detail below).

Sealable supports are resinous materials (usually synthetic polymers) which are capable of being sealed (or fused) to themselves or to another sheet of material using heat or ultrasonic pressure sealing techniques. Preferably, the supports are heat-sealable to themselves in an appropriate manner and in appropriate places to provide channels or voids between sealed sheets, mats or membranes.

The supports can be composed of, for example, polyesters {such as poly(ethylene terephthlate), poly[4,4'-(hexahydro-4,7-methanoindan-5-ylidene)diphenylene terephthlate] and poly(4,4'-isopropylidenediphenylene 1,1,3-trimethyl-3-phenyl-5,4'-indandicarboxylate)}, polycarbonates [such as biphenol A polycarbonate (for example, LEXAN™ sold by General Electric)], polyamides [such as poly(p-phenylene terephthalamide)], polyimides [such as the polyimide product of 4,4'-diaminodiphenylether and pyromellitic dianhydride], and celluloses [such as cellulose acetate, and cellulose acetate butyrate].

In one embodiment, sheets of polyethylene are sealed at the peripheral edges to form a container having voids for various reagents. In another embodiment, laminates of polyethylene and a polyester, such as poly(ethylene terephthalate), can be heat sealed. Laminates can have a variety of layers therein including adhesives or vapor barriers as well as sealable layers.

The detection deposits described herein are deposited on a surface of the sealable support in defined regions, and usually in a pattern of some type. Preferably, each detection deposit is in a defined region of the support surface such as in a round spot, and the deposits may comprise a particular arrangement of round spots.

Each detection deposit comprises a mixture of water-insoluble first and second particles which are prepared from the same or different polymers, glasses, ceramics, metals, or metal oxides (such as magnetic particles). Such particles are generally spherical in shape, although that is not critical as long as each deposit has the same type of particles, and therefore the same geometry, configuration and porosity. Where the particles are spherical, they generally have an average diameter of from about 0.001 to about 10 µm (preferably from about 0.1 to about 5 µm).

Preferably, the particles are prepared from a polymer (or composite of polymers) having a glass transition temperature ($T_{g1}$) of at least about 70° C. Preferably, the $T_{g1}$ is from about 70° to about 175° C., and more preferably it is in the range of from about 75° to about 140° C. Glass transition temperature refers to the temperature at which the polymer changes from a glassy state to a rubbery, flowing or tacky polymer. Procedures for measuring glass transition temperatures are described in *Techniques and Methods of Polymer Evaluation*, Vol. 1, Marcel Dekker, Inc., New York, 1966.

The particles useful herein are also impermeable and non-swellable in aqueous fluids. These properties insure structural integrity for the composition disposed on the support of the element. Non-swellability refers to particles exhibiting little swell (that is, less than 10% swell) in an aqueous fluid as measured using a swellometer of the type described by Green et al, *J.Photo.Sci.*, 20, 205 (1972), after immersion of the particles in an aqueous fluid at 38° C. for about 2.5 minutes.

The particles are generally composed of, at least on the surface thereof, naturally occurring or synthetic materials to which an oligonucleotide can be covalently attached (described below) to act as a capture probe. Such materials generally have reactive groups with which the oligonucleotide or a derivatized form thereof can be reacted to form a covalent bond.

In general, any reactive group with which an amino or sulfhydryl group is reactive is useful in this context. Particularly useful reactive groups include, but are not limited to, an active halogen, carboxy, amidine, activated 2-substituted ethylsulfonyl, activated 2-substituted ethylcarbonyl, vinylsulfonyl, vinylcarbonyl, epoxy, aldehyde, sulfhydryl, amino (after activation), hydrazine and active esters such as succinimidoxycarbonyl. Preferred particles are organopolymeric beads such as those described in EP-A-0 323 692 (published Jul. 12, 1989) prepared from one or more ethylenically unsaturated polymerizable monomers having an active halogen, activated 2-substituted ethylsulfonyl or vinylsulfonyl groups. Most preferred particles have reactive carboxy groups, as described in U.S. Pat. No. 5,147,777 (Sutton et al), incorporated herein by reference.

The monomers of the Sutton et al patent can be polymerized as homopolymers, but preferably they are copolymerized with one or more other ethylenically unsaturated polymerizable monomers.

More particularly, the particles useful in this invention are composed, at least on the surface thereof, of a polymer comprising:

(a) from about 0.1 to about 60 weight percent of recurring units derived from one or more ethylenically unsaturated polymerizable monomers having a reactive group as defined above, (b) from about 40 to about 99.9 weight percent of recurring units derived from one or more ethylenically unsaturated polymerizable monomers which, when homopolymerized, provide a water-insoluble homopolymer, and (c) from 0 to about 15 weight percent of recurring units derived from one or more ethylenically unsaturated polymerizable monomers other than those defined for components (a) and (b) above, including but not limited to hydrophilic monomers which provide colloidal stability to the copolymer.

Useful monomers for each component are described in the above noted Sutton et al patent.

Still other useful monomers for component (c) include those having polyoxyalkylene side chains as described for example in U.S. Pat. No. 5,086,143 (Sutton et al). Representative monomers, include but are not limited to, pentaethylene glycol monomethacrylate, decaethylene glycol monomethacrylate, eicosaethylene glycol monomethacrylate, pentaethylene glycol monoacrylate, polypropylene glycol monometh-acrylate and polypropylene glycol monomethacrylate.

Mixtures of various monomers for each component (a), (b) and (c) can be copolymerized as long as the monomers are compatible with each other and sufficient reactive groups are present on the surface of the resulting particles.

The copolymers useful herein to make the particles are prepared using standard emulsion or suspension polymerization techniques, as described for example by Sorenson et al in *Preparative Methods of Polymer Science*, 2nd Edition (1968), Wiley & Sons, New York, and Stevens, *Polymer Chemistry, An Introduction*, Addison Wesley Publishing Co., London (1975).

The particles can also be core/shell particles having the noted polymer described above as the shell so that reactive groups are available on the surface. Core/shell particles and procedures for making them are well known, as described for example in U.S. Pat. No. 4,401,765 (Craig et al) and U.S. Pat. No. 4,997,772 (Sutton et al). The core of such particles can be composed of any suitable polymer which contributes to the requisite physical integrity and glass transition temperature and is generally different from that of the shell polymer.

Molecules of an oligonucleotide are covalently attached to the particles as a capture probe for the target nucleic acid. Preferably, the capture probe is complementary and specific to a nucleic acid sequence of one of the strands of a target double-stranded nucleic acid.

The oligonucleotide is covalently attached to the polymeric particles using any suitable technique. They can be directly attached by reacting the reactive groups on the surface of the particles with corresponding sulfhydryl, carboxy or amino groups of the oligonucleotide. Alternatively, the oligonucleotide can be biotinylated or otherwise modified to add a specific binding species which can then specifically bind with its corresponding receptor which can be attached to the particles. Avidin-biotin complexes are known to be used for this purpose as described for example in EP-A-0 139 489 (published May 2, 1985), EP-A-0 192 168 (published Aug. 27, 1986) and EP-A-0 370 694 (published Jul. 24, 1991). Incorporating biotin into an oligonucleotide can be achieved using known technology including that described in EP-A-0 097 373 (published Jan. 4, 1984).

Preferably, however, it is desired to chemically modify the oligonucleotide in order to provide reactive groups therein or to provide "spacer" groups or "linker" groups to extend the oligonucleotide away from the surface of the particles. Techniques for doing this are well known, as described for example, in U.S. Pat. No. 4,914,210 (Levenson et al) and WO 89/11548 (published Nov. 30, 1989).

The coverage of oligonucleotide on the surface of the particles may vary depending upon the size of the particles, the chemical means of attachment, the length of the oligonucleotide, and the length of any spacer molecule.

The particles containing the capture probe can be dried down on a support. Alternatively, a polymeric adhesive can be used to affix the particles to the support. It also acts to bond the particles to each other. This adhesive comprises a polymer which has a glass transition temperature ($T_{g2}$) which is at least about 30° C. less than the glass transition temperature ($T_{g1}$) of the polymer of the particles. Preferably, $T_{g2}$ is from about 30° to about 120° C. less than $T_{g1}$. $T_{g2}$ is also less than about 90° C. More preferably, $T_{g2}$ is in the range of from about −50° to about +40° C.

The adhesive is insoluble in aqueous fluids commonly encountered in diagnostic and analytical methods. While it is not essential, it is also preferred that the adhesive be non-swellable in aqueous fluids.

More particularly, the adhesive polymer is composed of:

(d) from about 55 to 100 weight percent of recurring units derived from one or more ethylenically unsaturated polymerizable monomers used in component (b) of the first polymer described above, (e) from 0 to about 45 weight percent of recurring units derived from one or more ethylenically unsaturated monomers which form a water soluble homopolymer, or which provide hydrophilicity from polar groups [such as primary, secondary and tertiary amines, hydroxy and poly(alkyleneoxy) groups], anionic groups [such as carboxylate, sulfonate, sulfate, phosphate and phosphonate], and cationic groups [such as trialkylammonium and trialkylphosphonium] and others readily apparent to one skilled in the art, and (f) from 0 to about 15 weight percent of recurring units derived from one or more ethylenically unsaturated monomers which can provide crosslinking in the polymer adhesive.

While the monomers described above for component (b) of the first polymer are useful also in component (d), the preferred monomers for component (d) are alkyl acrylates and methacrylates wherein the alkyl group has from 1 to 8 carbon atoms (such as methyl, ethyl, n-propyl, n-butyl, isobutyl, 2-ethylhexyl, hexyl and octyl), and which alkyl group can also be interrupted with one or more thio, oxy or iminoalkyl groups having 1 to 6 carbon atoms. More preferred monomers include, but are not limited to, methyl acrylate, methyl methacrylate, n-butyl acrylate and n-butyl methacrylate. Methyl acrylate is most preferred.

Useful monomers for component (e) include, but are not limited to, charged monomers (cationic or anionic) such as acids and salts thereof, including but not limited to, acrylic acid, methacrylic acid, itaconic acid, 2-acrylamido-2-methylpropanesulfonic acid, 3-methacryloyloxypropane-1-sulfonic acid and their salts, N-(2-acryloyloxyethyl-N,N,N-trimethylammonium methosulfate, 3-hydroxyethyl-1-vinylimidazolium chloride, aminoethylmethacrylate hydrochloride, N-(2-aminopropyl)methacrylamide hydrochloride, 2-carboxyethyl acrylate, p-styrene sulfonic acid and salts thereof, m & p-carboxymethylstyrene and its salts, and other ethylenically unsaturated polymerizable sulfonates, carboxylates, sulfates, phosphonates, quaternary ammonium salts, pyridinium salts, imidazolium salts, quinoxalinium salts, and other salts readily apparent to one skilled in the art. Also useful are the carboxy-containing monomers (and salts thereof) described above for component (a) of the particle polymer.

Nonionic monomers which also are useful in component (e) include, but are not limited to, amine-containing monomers, such as dimethylaminopropyl acrylate and diethylaminoethyl methacrylate and hydroxy-containing monomers such as 2-hydroxyethyl acrylate, 2-hydroxyethyl methacrylate, 2,3-dihydroxypropyl acrylate, pentaethylene glycol monoacrylate and others readily apparent to one skilled in the art.

Preferred monomers in component (e) include 2-acrylamido-2-methylpropanesulfonic acid and salts thereof, 2-aminoethyl methacrylate hydrochloride and N-(2-aminopropyl)methacrylamide hydrochloride.

The monomers for component (f) which can provide crosslinking can either be crosslinked during polymerization, or provide crosslinking after subsequent chemical reaction with themselves or with additional crosslinking agents. Such monomers include multifunctional vinyl monomers such as di- and triacrylates and methacrylates (such as ethylene diacrylate and ethylene dimethacrylate), divinylbenzenes, and monomers containing active methylene groups which can be crosslinked using known chemical reactions. Examples of the latter include 2-acetoacetoxyethyl methacrylate, N-(2-acetoacetoxyethyl)acrylamide, N-(2-acetoacetamidoethyl)methacrylamide, 6-(m & p-vinylphenyl)-2,4-hexanedione, ethyl acryloylacetate and other similar monomers known in the art, such as those described in U.S. Pat. No. 3,554,987 (Smith), U.S. Pat. No. 3,459,790 (Smith) and U.S. Pat. No. 4,247,673 (Ponticello et al).

Preferred monomers for component (f) include 2-acetoacetoxyethyl methacrylate, N-(2-acetoacetoxyethyl)acrylamide and N-(2-acetoacetamidoethyl)methacrylamide.

Preferably, the copolymers useful in preparing the adhesive are composed of recurring units derived from about 70 to about 98 weight percent of component (d), from about 2 to about 30 weight percent of component (e), and from 0 to about 10 weight percent of component (f). More preferably, they are composed of recurring units derived from about 85 to about 95 weight percent of component (d), from about 2 to about 15 weight percent of component (e), and from 0 to about 8 weight percent of component (f).

A preferred addition polymer for the adhesive is poly[methyl acrylate-co-2-acrylamido-2-methylpropanesulfonic acid, sodium salt-co-2-acetoacetoxyethyl methacrylate].

The polymers useful as adhesives can be prepared using conventional emulsion polymerization techniques, for example as described in the literature cited above for preparation of the particle polymer.

The detection deposits also contain what are identified as "second" particles which have the same or different composition as the particles carrying the capture probe, but the second particles are free of capture probe. Generally, such particles are of the same average diameter and shape as the first particles. Also, such second particles are preferably of the same composition and size as the first particles, and therefore differ only in the absence of capture probe on the surface thereof.

Thus, preferably each detection deposit has a mixture of first and second particles, and polymer adhesive. There is a varying weight ratio of the first particles to the second particles from one detection deposit to another on the support. Generally, a detection deposit is prepared from a 0.5 to 4 μl sample of particles and adhesive at from about 0.1 to about 10% solids. The first particles can have from about 0.1 to 100% saturation of capture probe.

The polymer adhesive can be present in each detection deposit in an amount of up to about 20% by weight (based on the dry weight of the particles and capture probe). Preferably, the adhesive is present in an amount of from about 0.1 to about 20% by weight, with an amount of from about 0.2 to about 10 weight percent being more preferred. The term "about" refers to plus or minus 20% of the noted value.

A detection deposit can optionally contain other addenda, such as buffers, surfactants or binders in minor amounts, that is, generally less than about 5% of the total weight of the deposit.

The detection deposit can be applied to the support in any suitable manner. For example, it can be coated thereon using standard coating equipment and techniques, applied by hand, printed thereon, spotted with a pipette tip, microsyringe tip or microdispensing pump, and then dried. Preferably, however, it is disposed in an aqueous suspension with a microsyringe tip and dried on a support. Drying is accomplished by heating the aqueous suspension in a range of from about 10° to about 80° C. less than the glass transition temperature of the polymer described above used to prepare the particles.

To enhance adhesion of the detection deposit to supports which are generally hydrophobic, it may be desirable to pretreat the support to render it more hydrophilic. The pretreatments can be of a chemical, electrical or mechanical nature, or a combination of different types of treatments. For example, chemical treatments include the use of chromic acid which involves etching a surface with sodium dichromate in sulfuric acid for a few minutes.

The support can also be treated with activated species in gases, such as noble gases, as described for example in U.S. Pat. No. 3,526,583 (Hayward) and by Hanson et al, *Chem. & Eng. News*, 44, pages 58–59, Sep. 26, 1966. Still another known procedure is the use of nitrous oxide at elevated temperatures.

Electrical treatments include corona discharge, flaming and electrode discharge processes which are also well known in the art, for example as described in *Adhesive Bonding*, Lee (Ed.), Plenum Press, New York, pages 265–267.

Another pretreatment involves simultaneous chemical and electrical treatment such as with a radio frequency electromagnetic field in the presence of a reactive gas. Details of such procedures are provided for example in U.S. Pat. No. 3,761,229 (Lidel) and U.S. Pat. No. 4,072,769 (Lidel).

While other chemical, electrical and mechanical pretreatments would be readily apparent to one skilled in the art, preferred pretreatments include corona discharge treatment, chromic acid treatment and treatment with a radio frequency electromagnetic field in the presence of a reactive gas. Corona discharge treatment is most preferred.

Alternative or supplemental to the pretreatments described above, a hydrophilic polymer can be applied to the support to act as a hydrophilic subbing layer. Subbing layer polymers and methods for their preparation are well known in the art, for example as described in U.S. Pat. No. 3,143,421 (Nadeau et al) and U.S. Pat. No. 3,201,249 (Pierce et al). Generally, such polymers are composed of recurring units having one or more pendant anionic or hydrophilic groups such as carboxy, sulfonyl, phosphono, phosphinyl, carbonyl and hydroxy. Other general characteristics of such polymers include, but are not limited to, the presence of some halogen content from monomers such as vinyl chloride, vinylidene dichloride and others readily apparent to one skilled in the art.

Particularly useful subbing layer materials include poly-(acrylonitrile-co-vinylidene chloride-co-acrylic acid), poly-(methyl acrylate-co-vinylidene chloride-co-itaconic acid), poly(monomethyl itaconate-co-vinylidene chloride), poly-(monoethyl itaconate-co-vinylidene chloride) and poly-(monobutyl itaconate-co-vinylidene chloride).

The test element of this invention can be prepared by disposing a suspension of particles, capture probe and polymer adhesive on a suitable support as defined herein, and heating the disposed composition at a temperature and for a time sufficient to dry the suspension and form a detection deposit. While the time and temperature for suitable adhesion can be varied inversely, in general, a temperature in the range of from about 10° to about 80° C. less than the glass transition temperature of the first polymer is used. The time for heating is generally from about 10 to about 40 seconds. Several such deposits can be provided in this fashion to form an array of detection deposits in any suitable arrangement. Generally, each detection deposit is a circular spot on the support.

In a preferred test element, there are from two to ten detection deposits arranged in an order of from the least to the most amount of the first particles having capture probe or from the most to the least amount of the first particles having capture probe. Most preferably, the target nucleic acid is contacted first with the deposit having the least amount of the first particles having capture probe.

For example, one or more rows of deposits with increasing or decreasing amounts of first particles can be arranged on a support which is a channel of a test device, such as that described, for example, in U.S. Pat. No. 5,173,260 or U.S. Pat. No. 5,229,297 (both noted above). Fluid can be passed in the channel over the deposits to capture target nucleic acid.

A test kit of this invention can include the test element described herein and one or more hybridization assay or amplification reagents. Such reagents are well known in the art, and some of them are described specifically in the teaching hereinabove. The kit can also include a labeled receptor molecule for the specific binding ligand used in the assay. Various pieces of assay equipment, test packs and instructions can also be included in the kit, as one skilled in the art would readily expect.

The following example is included to illustrate the practice of this invention, and is not meant to be limiting in any way. All percentages are by weight unless otherwise noted.
Materials and Methods for Examples:

Recombinant DNA polymerase from *Thermus aquaticus* was prepared using known procedures, such as that described in U.S. Pat. No. 4,889,818 (noted above).

The oligonucleotides used herein were prepared using known starting materials and procedures using an Applied Biosystems Model 380B, three column DNA synthesizer using standard phosphoramidite chemistry and the ABI 1 μmolar scale, fast cycle protocol. Nucleoside-3'-phosphoramidites and nucleoside derivatized controlled pore glass supports were obtained from Applied Biosystems. The capture probe was functionalized at the 3' end with two tetraethylene glycol spacers followed by a single aminodiol linking group according to U.S. Pat. No. 4,914,210 (Levenson et al) and U.S. Pat. No. 4,962,019 (Levenson et al). All purifications were carried out using a nucleic acid purification column, followed by reverse phase HPLC techniques.

The capture probe used in Example 1 had the following sequence:

SEQ ID NO:1: 5'-GAACCGAGGG CCGGCTCACC TCTATGTTGG-X-3' wherein X is the functionalized terminal group described above.

An oligonucleotide which is complementary to SEQ ID NO:1: was used as a target nucleic acid in Example 1. It had the following sequence:
SEQ ID NO:2: 5'-CCAACATAGA GGTGAGCCGG CCCTCGGTTC-Y-3' wherein Y comprises two tetraethylene glycol units attached to a single biotin phosphoramidite using the procedures of the Levenson et al patents noted above. Thus, the target nucleic acid was labeled with a biotin derivative for detection after capture.

Deoxyribonucleotides (dNTP's) were obtained from Sigma Chemical Co.

A streptavidin-peroxidase conjugate solution comprised a commercially available (Zymed Laboratories, Inc.) conjugate of avidin and horseradish peroxidase (126 μl/l), casein (0.5%) and merthiolate (0.5%).

The dye-providing composition (pH 6.8) contained 4,5-bis(4-dimethylaminophenyl)-2-(4-hydroxy-3-methoxyphenyl)imidazole (0.005%), poly(vinyl pyrrolidone) (1%), diethylenetriaminepentaacetic acid (10 μmolar), and sodium phosphate buffer (5 mmolar).

Particulate capture probes were prepared by attaching the oligonucleotide capture probe to particles of poly[styrene-co-3-(p-vinylbenzylthio)propionic acid] (95:5 weight ratio, 1 μm average diameter) in the following manner. A suspension of the particles in water was washed twice with 2-(N-morpholino)ethanesulfonic acid buffer (0.1 molar, pH 6), and suspended to approximately 10% solids. A sample (3.3 ml) of the washed particles, diluted to 3.33% solids in the buffer (0.1 molar), was mixed with 1-(3-dimethylaminopropyl)-3-ethylcarbodiimide hydrochloride (2.1 ml of 84 mg/ml water) and the appropriate probe (983 μl of 44.44 OD/ml nanopure water). The resulting suspension was heated at 50° C. in a water bath for about two hours with intermittent mixing and centrifuged. The particles were washed three times with tris(hydroxymethyl)aminomethane buffer (0.01 molar, pH 8) containing (ethylenedinitrilo)tetraacetic acid disodium salt (0.0001 molar) and resuspended therein to 4% solids.

In Example 1, the particulate capture probes were mounted on uncoated LOPRODYNE™ polyamide microporous membranes (Pall Corp., 5 μm average pore size) in test wells of SURECELL™ test devices (Eastman Kodak Company).

Other reagents and materials were obtained either from commercial sources or prepared using readily available starting materials and conventional procedures.

EXAMPLE 1

Preparation of Test Element and Detection of Target Nucleic Acid

This example demonstrates the preparation of a test element of this invention and its use for semi-quantitative detection of a target nucleic acid. The particles used in this examples are those described above prepared from poly [styrene-co-3-(p-vinylbenzylthio)propionic acid] (95:5 weight ratio).

The resulting dispersion of capture probe on polymeric particles ("first" particles) was mixed with the same particles ("second" particles) having no capture probe to form aqueous dispersions having 0.25% total solids, but varying weight ratios of the particles having capture probe and particles having no capture probe. In the suspensions, 0.0001, 0.0002, 0.0009, 0.0039 or 0.0625% of the total particles were first particles having capture probe. One suspension of the second particles only (no capture probe) was used to provide a Control detection deposit.

Samples (2 μl) of each suspension were applied to the surfaces of an uncoated LOPRODYNE™ polyamide microporous membranes in test wells of the SURECELL™ test devices and allowed to dry to form dried detection deposits of different concentrations of first and second particles in the test device. A Control deposit containing no capture probe was similarly formed.

Test solutions were prepared containing various concentrations (0.08, 0.31, 1.25, 5 and 10 pmole/ml) of the target nucleic acid, tris(hydroxymethyl)aminomethane hydrochloride buffer (pH 8, 10 mmolar), potassium chloride (50 mmolar), magnesium chloride (10 mmolar) and gelatin (1 mg/ml).

A sample (95 μl) of each test solution was added to the test wells of the SURECELL™ test devices containing the detection deposits (one sample per well), and incubated at 42° C. for five minutes to allow hybridization of capture probe and target nucleic acid. The deposits were then washed at 55° C. with 250 μl of the buffer noted above.

The conjugate solution (50 μl) was then added to each test well. Incubation at room temperature was allowed for two minutes so the conjugate would complex with the biotinylated target nucleic acid. Unbound materials were then washed away at 55° C. with the same buffer noted above (250 μl).

The dye-providing composition (100 μl) described above was then added to the test wells, followed by two minutes of incubation at room temperature. Dye formation was quenched by adding a solution (100 μl) of sodium azide (0.1%). The resulting dye signal was visually evaluated using a color chart having values from 0 to 10 with 10 representing the highest dye density. The results are shown in the bar graphs of the FIGURE for the three lowest concentrations of target nucleic acid. In each series of three bars on the graph, the first bar was the signal for 1.25 pmole/ml (bars A, D and G), the second bar was the signal for 0.31 pmole/ml (bars B, E and H), and the third bar (bars C, F and I) was the signal for 0.08 pmole/ml target nucleic acid, respectively.

Semi-quantitative detection of the target nucleic acid at the three concentrations was achieved because of the combination of signal generation and capture probe dilution. The differences in signal intensity could readily be determined in proportion to the relative amounts of target nucleic acid in the test specimens.

This example demonstrates the practice of the present invention to detect a synthethically prepared target nucleic acid which has been added to a test specimen. The invention would be equally useful if the target nucleic acid had been from a natural source, whether amplified or not, as described herein. The source of the target nucleic acid is irrelevant for the detection method of this invention.

The invention has been described in detail with particular reference to preferred embodiments thereof, but it will be understood that variations and modifications can be effected within the spirit and scope of the invention.

We claim:

1. A method for the semi-quantitative determination of a target nucleic acid comprising:

A) contacting a target nucleic acid having a specific binding ligand bound thereto with a water-insoluble support having affixed thereon a multiplicity of detection deposits, each detection deposit comprising a mixture of water-insoluble first and second particles, said first particles having affixed thereto a capture probe which is specific to and hybridizable with said target nucleic acid, and said second particles being free of all capture probes, said multiplicity of detection deposits having a varying weight ratio of said first particles to said second particles, but all of said detection deposits having about the same total weight of polymeric particles and the same configuration, to capture said target nucleic acid strand on said detection deposits in proportion to the amount of said first particles in each detection deposit, B) contacting said captured target nucleic acid strand in said detection deposits with a receptor for said specific binding ligand, said receptor being labeled with a reporter molecule, to complex said reporter labeled receptor with said captured target nucleic acid strand and thereby capture said reporter labeled receptor on each of said detection deposits in proportion to the amount of captured ligand labeled target nucleic acid strand in each of said detection deposits, and C) detecting the reporter molecules on said detection deposits as a semi-quantitative determination of the presence of said target nucleic acid in a range of 0.08 to 1.25 pmol/ml nucleic acid.

2. The method of claim 1 wherein said specific binding ligand is biotin, and said receptor is streptavidin which is labeled with a radioisotope, chemiluminescent reagent or enzyme.

3. The method of claim 2 wherein said streptavidin is labeled with a peroxidase.

4. The method of claim 1 wherein said target nucleic acid having said ligand bound thereto is contacted with from two to ten detection deposits in step B, in order of the detection deposit having the least amount of said first particles to the detection deposit having the most amount of said first particles.

5. The method of claim 1 wherein said first and second particles have about the same average diameter.

6. The method of claim 1 wherein, simultaneously with contact of said target nucleic acid with said detection deposits, said target nucleic acid is hybridized with a detection probe conjugated with said specific binding ligand.

7. A method for the amplification and semi-quantitative determination of a target nucleic acid comprising:

A) amplifying opposing strands of a target nucleic acid with a DNA polymerase, more than one dNTP and a set of two primers specific to and hybridizable with said opposing strands, one of said primers being labeled with a specific binding ligand, thereby providing at least one amplified ligand labeled strand of said target nucleic acid, B) contacting said amplified ligand labeled target nucleic acid strand with a water-insoluble support having affixed thereon a multiplicity of detection deposits,
each detection deposit comprising a mixture of water-insoluble first and second particles,
said first particles having affixed thereto a capture probe which is specific to and hybridizable with said ligand labeled target nucleic acid strand, and
said second particles being free of all capture probes,
said multiplicity of detection deposits having a varying weight ratio of said first particles to said second particles, but all of said detection deposits having about the same total weight of polymeric particles and the same configuration,
to capture said ligand labeled target nucleic acid strand on said detection deposits in proportion to the amount of said first particles in each detection deposit, C) contacting said captured ligand labeled target nucleic acid strand in said detection deposits with a receptor for said specific binding ligand, said receptor being labeled with a reporter molecule,
to complex said reporter labeled receptor with said captured ligand labeled target nucleic acid strand and thereby capture said reporter labeled receptor on each of said detection deposits in proportion to the amount of captured ligand labeled target nucleic acid strand in each of said detection deposits, and D) detecting the reporter molecules on said detection deposits as a semi-quantitative determination of the presence of said target nucleic acid in a range of 0.08 to 1.25 pmol/ml nucleic acid.

8. The method of claim 7 wherein said specific binding ligand label on said primer is biotin.

9. The method of claim 8 wherein amplification is carried out using a thermostable DNA polymerase, each of dATP, dCTP, dGTP and dTTP and a DNA polymerase cofactor, said receptor is streptavidin, and said reporter molecule is a peroxidase which is detected by contact with one or more reagents which provide a colorimetric signal in response to the reaction of peroxidase with a substrate.

10. The method of claim 7 wherein amplification is carried out with from 20 to 50 polymerase chain reaction cycles.

11. The method of claim 7 wherein said first and second particles have about the same average diameter, and said ligand labeled target nucleic acid is contacted with from two to ten detection deposits in step B, in order of the detection deposit having the least amount of said first particles to the detection deposit having the most amount of said first particles.

12. A test element comprising a water-insoluble support having affixed thereon a multiplicity of detection deposits,
each detection deposit comprising a mixture of water-insoluble first and second particles,
said first particles having affixed thereto a capture probe which is specific to and hybridizable with a ligand labeled target nucleic acid, and
said second particles being free of capture probes,
said multiplicity of detection deposits having a varying weight ratio of said first particles to said second particles, but all of said detection deposits having about the same total weight of polymeric particles and the same configuration.

13. The test element of claim 12 wherein said support is a polymeric membrane, filter paper, fibrous mat, resin-coated film or paper or uncoated film or paper.

14. The test element of claim 12 wherein said support is heat or ultrasonic sound sealable resin-coated paper or polymeric film which has been pretreated by corona discharge or by application of a resinous hydrophilic subbing layer.

15. The test element of claim 12 wherein each of said detection deposits comprises a polymeric adhesive present in an amount of up to about 20 weight % of the total dry weight of each of said detection deposits.

16. The test element of claim 12 having from two to ten detection deposits which are circular spots on said support.

17. A kit for the detection of a target nucleic acid labeled with a specific binding ligand comprising:

a) either an amplification reagent, or a reporter labeled receptor for said specific binding ligand, and b) a test element comprising a water-insoluble support having affixed thereon a multiplicity of detection deposits,
each detection deposit comprising a mixture of water-insoluble first and second particles,
said first particles having affixed thereto a capture probe which is specific to and hybridizable with a ligand labeled target nucleic acid, and
said second particles being free of capture probes,
said multiplicity of detection deposits having a varying weight ratio of said first particles to said second particles, but all of said detection deposits having about the same total weight of polymeric particles and the same configuration.

18. The test kit of claim 17 comprising one or more amplification reagents, and wherein said test element has from two to ten detection deposits which are circular spots on said support, and said first and second particles having about the same average diameter.

19. The test kit of claim 18 comprising a thermostable DNA polymerase, a cofactor for said DNA polymerase, each of dATP, dCTP, dGTP and dTTP, streptavidin labeled with peroxidase, and at least one primer which is specific to and hybridizable with said target nucleic acid, said primer being labeled with biotin.

20. The test kit of claim 17 wherein said support is a heat or ultrasonic sound sealable material which has been pretreated by corona discharge or by application of a hydrophilic subbing layer, and each of said detection deposits comprising a polymeric adhesive which is present in an amount of up to about 20 weight % of the total dry weight of each of said detection deposits.

* * * * *